US008559006B2

(12) United States Patent  
Penney et al.

(10) Patent No.: US 8,559,006 B2
(45) Date of Patent: Oct. 15, 2013

(54) PARTICULATE DETECTOR

(75) Inventors: Stephen John Penney, Middlesex (GB); John E. A. Shaw, Middlesex (GB); Paul J. Taylor, Woking (GB); Steven Ian Bennett, Middlesex (GB)

(73) Assignee: Thorn Security Limited, Sunbury-on-Thames, Middlesex (GB)

( * ) Notice: Subject to any disclaimer, the term of this patent is extended or adjusted under 35 U.S.C. 154(b) by 373 days.

(21) Appl. No.: 13/121,467

(22) PCT Filed: Oct. 1, 2009

(86) PCT No.: PCT/GB2009/002339
§ 371 (c)(1),
(2), (4) Date: Mar. 29, 2011

(87) PCT Pub. No.: WO2010/038024
PCT Pub. Date: Apr. 8, 2010

(65) Prior Publication Data
US 2011/0181870 A1    Jul. 28, 2011

(30) Foreign Application Priority Data

Oct. 1, 2008 (GB) .................................. 0817972.3

(51) Int. Cl.
*G01N 21/00*    (2006.01)
*G01J 1/42*    (2006.01)
(52) U.S. Cl.
USPC .......................................... 356/337; 356/222
(58) Field of Classification Search
USPC ................................................ 356/335–344
See application file for complete search history.

(56) References Cited

U.S. PATENT DOCUMENTS 4,642,471 A * 2/1987 Guttinger et al. ............. 250/574
4,728,801 A   3/1988 O'Connor
(Continued)

FOREIGN PATENT DOCUMENTS

| DE | 3821543 A1 | 1/1989 |
| GB | 2 319 605 A | 5/1998 |
| GB | 2 379 977 A | 3/2003 |
| JP | 2000356583 | 12/2000 |

OTHER PUBLICATIONS

Miyata T et al, Temporal Emission Characteristics of Pulse-Driven and Sinusoidally-Modulated White Light-Emitting Diodes, The 5th Pacific Rim Conference on Lasers and Electro-Optics, Dec. 15-19, 2003, Piscataway, New Jersey, USA, IEEE, vol. 2, Dec. 15, 2003, pp. 645-645, XP010690071, ISBN: 978-0-7803-7766-0 (1 pg).

(Continued)

*Primary Examiner* — Gregory J Toatley
*Assistant Examiner* — Jarreas C Underwood

(57) ABSTRACT

A particulate detector (10) comprises a radiation source (12) arranged to emit radiation in at least first and second predetermined wavebands towards a sampling region (18) suspected of containing particulates, and a detection element (14), shielded from the radiation source (12), and arranged to detect radiation from the sampling region (18) at least first and second instances. The radiation source (12) is such that the emissions in the wavebands temporarily overlap. The detector is such that, at the instances at which the radiation is detected, the relative contributions from the emissions in each predetermined waveband are distinguishable, thereby allowing characteristics of the particulates to be determined. The radiation source (12) may comprise a light emitting diode (24).

15 Claims, 11 Drawing Sheets

(56) References Cited

U.S. PATENT DOCUMENTS

| | | | |
|---|---|---|---|
| 6,225,910 B1* | 5/2001 | Kadwell et al. | 340/630 |
| 6,965,205 B2* | 11/2005 | Piepgras et al. | 315/318 |
| 7,142,105 B2* | 11/2006 | Chen | 340/521 |
| 7,233,253 B2* | 6/2007 | Qualey, III | 340/628 |
| 2007/0285263 A1 | 12/2007 | Qualey, III | |
| 2012/0140231 A1* | 6/2012 | Knox et al. | 356/442 |

OTHER PUBLICATIONS

Shiina T et al, Modulated White-LED Interferometer, Proceedings of the SPIE—The International Society for Optical Engineering SPIE-INT. Soc. Opt. Eng USA, vol. 4920, 2002, pp. 174-181, XP002558252, ISSN: 0277-786X, p. 178-p. 179, Figures 6,7 (8 pgs).

Okamura Y et al, Chartacteristics of Modulated White-LED and Their Application to Electrically Controlled Spectroscopy, Proceedings of the SPI—The International Society for Optical Engineering SPIE-Int. Soc. Opt. Eng USA, vol. 4922, 2002, pp. 43-50, XP002558253, ISSN: 0277-786X, Abstract, p. 49-p. 50, Figures 2-4 (8 pgs).

International Searching Authority, International Search Report and Written Opinion dated Dec. 14, 2009 for International Application No. PCT/GB2009/002339, International Filing Date Oct. 1, 2009 (12 pgs).

European Patent Office, Communication Pursuant to Rules 161(1) and 162 EPC, dated May 20, 2011, in the related European National Stage Patent Application No. EP 09785183.6.

Withers & Rogers LLP, Amendments filed on Jul. 19, 2011, in response to the European Patent Office, Communication Pursuant to Rules 161(1) and 162 EPC, dated May 20, 2011, in the related European National Stage Patent Application No. EP 09785183.6.

* cited by examiner

PARTICULATE DETECTOR

RELATED APPLICATION

This is the U.S. National Stage Application of International Application PCT/GB2009/002239 filed Oct. 1, 2009, which claims priority to British patent application GB 0817972.3 filed Oct. 1, 2008. The entire teachings of the above applications are incorporated herein by reference.

This invention relates to a particulate detector and, in particular, to a detector operating in the optical region of the electromagnetic spectrum.

Particulate detectors are commonly used in known smoke alarms and fire alarms to detect smoke particles in the air caused by a fire. In such a detector, radiation is emitted from a light source, towards a region known as a sampling region. If particulates are present in the sampling region, some of the radiation incident on the sampling region is deflected by particulates in the region towards a detection element. In a scatter detector, the detection element detects the radiation that has been scattered by the particulates. In a transmission detector, the detection element detects the radiation that is transmitted through the sampling region, and not scattered by the particulates. In a scatter detector, the detector element is shielded from the light source, so that radiation from the light source only reaches the detector element if it has been deflected in the sampling region. Detectors of this type rely on the concept of Mie theory, which can be used to explain radiation scattering by an isotropic sphere embedded in a homogeneous medium. For a particular wavelength of radiation, the angle of scattering is proportional to the size of the particulate from which the radiation is scattered. The detection element will be arranged such that, when the sampling region is occupied by substantially clean air, a relatively small amount of scattered radiation is detected. However, when particulates, for example particulates of smoke or dust, are present in the sampling region, for a given wavelength the radiation will be scattered through a different angle and, therefore, more radiation will be detected by the detection element. The detection element outputs a signal to a processor which analyses the amount of scattered radiation reaching the detection element; and, if this amount of radiation exceeds a predetermined value, the processor triggers an alarm, on the assumption that smoke has caused the scattering of the radiation. The disadvantage of such a detector is that no distinction is made between smoke and any other airborne particulates which could cause the scattering, for example, steam, dust or dry ice.

It is an aim of the present invention to provide an improved particulate detector, which is compatible with existing detection systems and detector components, and which overcomes, or at least mitigates, the above-mentioned problems of the prior art.

In a first aspect of the present invention, a particulate detector comprises a radiation source arranged to emit radiation in at least first and second predetermined wavebands towards a sampling region, and a detection element arranged to detect radiation from the sampling region at least first and second instances, wherein the radiation source is such that the emissions in the at least first and second predetermined wavebands temporarily overlap, and wherein the detector is such that, at the instances at which the radiation is detected, the relative contributions from the emissions in each predetermined waveband are distinguishable, thereby allowing characteristics of the particulates in the sampling region to be determined.

An advantage of the temporal overlap is that radiation in the wavebands will pass through substantially the same volume from the radiation source to the detection element, and the positions of the particulates in that volume will remain substantially unchanged during the time taken for the radiation to pass through. The characteristics of the particulates that are determinable from the detected radiation may be, conveniently, size, shape, density and/or mass.

Preferably, the radiation emitted in the first predetermined waveband is emitted in a pulse and, more preferably, the pulse is a square pulse.

Advantageously, the first instance at which radiation is detected occurs after the start of the pulse but before the end of the pulse, and the second instance occurs after the end of the pulse. More advantageously, the temporal separation, or the time, between the at least first and second instances is relatively small compared to the duration of the pulse. Ideally, the temporal separation between the at least first and second instances is sufficiently small, such that particulates in the sampling region do not move a significant amount between the measurements being taken. That way, the positions of the particulates in the sampling region will remain substantially unchanged during the time taken for the radiation to pass through.

Preferably, the detector further comprises a processor arranged to process information about the radiation received by the detection element. The processor is conveniently arranged to calculate a ratio of the amplitudes of the received signals at each instance, and uses the amplitude ratios to determine characteristics of and, hence, ultimately the identity of, the particulates.

Preferably, the radiation source comprises a light emitting diode for emitting radiation in the first predetermined waveband. Preferably, the light emitting diode is arranged to emit radiation having a waveband in the range 200 nm to 800 nm, more preferably in the range 350 nm to 600 nm, and most preferably in the range 450 nm to 500 nm.

Advantageously the radiation source further comprises a phosphor layer arranged to absorb at least some of the radiation in the first predetermined waveband, and to emit radiation in the second predetermined waveband. Alternatively, the radiation source may comprise a second light emitting diode for emitting radiation in the second predetermined waveband. Advantageously, the radiation emitted in the first predetermined waveband is used to power the second light emitting diode. An advantage of the radiation emitted in the first predetermined waveband causing the emission to occur from the phosphor layer or the second light emitting diode is that only one signal pulse is required; to power the radiation source to cause the emission in the first predetermined waveband.

Preferably, the detector further comprises an optical bleed channel for enabling radiation emitted by the radiation source to pass directly to the detection element. An advantage of the optical bleed channel is to provide optical and electrical communication between the radiation source and the detection element. This enables the ratio of received signals in different wavebands to be monitored over time, and also enables calibration of the detector.

The detector may be a scatter detector, in which the detection element is arranged to detect radiation which is scattered from particulates in the sampling region, or a transmission detector, in which the detection element is arranged to detect radiation which passes directly though the sampling region.

In another aspect of the present invention, a detector system comprises a control unit and a plurality of detectors, each of which is as described herein.

Advantageously, the control unit is arranged to supply power to, and receive signals from, each detector. The control unit is preferably also arranged to receive signals from at least one additional detection device, and combine information received from the or each additional detection device with information received from at least one of the detectors. Advantageously, each additional detection device is one of the following group: a heat sensor; a gas sensor; a moisture sensor.

Conveniently, the control unit includes a processor arranged to process information received by the control unit from the plurality of detectors. The processor in the control unit is conveniently arranged to calculate a ratio of the amplitudes of the received signals at each instance, and uses the amplitude ratios to determine characteristics of and, hence, ultimately the identity of, the particulates. Alternatively, the processing may be carried out by both a processor in one or more of the plurality of detectors and by the processor in the control unit.

In yet another aspect of the present invention, a method of detecting particulates dispersed in a fluid comprises the steps of:
  providing a particulate detector having a radiation source and a detection element;
  emitting radiation having wavebands in at least first and second predetermined wavebands from the radiation source, the emissions being temporarily overlapped; and
  detecting radiation at each distinct waveband that has been scattered by the particulates.

In yet another aspect of the present invention, a method of detecting particulates dispersed in a fluid comprises the steps of:
  providing a particulate detector having a radiation source and a detection element;
  emitting radiation having wavebands in at least first and second predetermined wavebands from the radiation source, the emissions being temporarily overlapped; and
  detecting radiation at each distinct waveband that has been transmitted through the particulates.

Advantageously, the method further comprises the step of processing information about the detected radiation, so as to determine characteristics of the particulates and, thereby determine the identity or identities of the particulates.

The invention will now be described in greater detail, by way of example, with reference to the drawings, in which.

Figure 1:
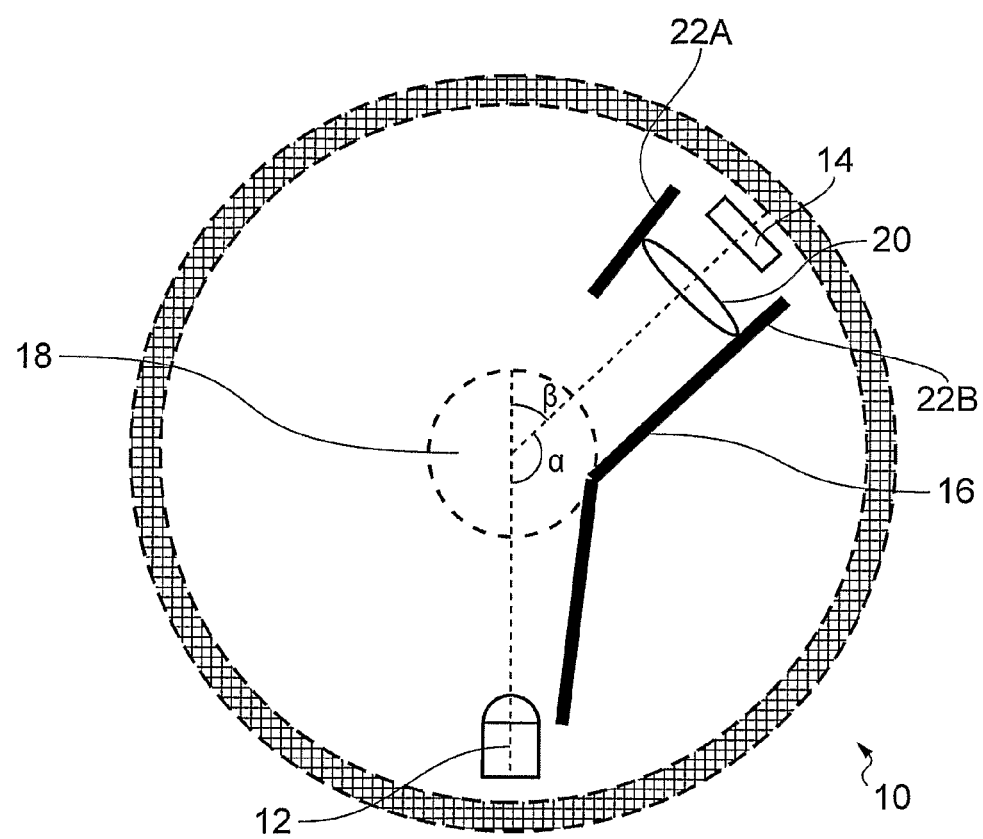
FIG. 1 is a schematic diagram of a detector constructed according to the invention.

Referring to the drawings, FIG. 1 shows an optical scatter detector 10. The detector 10 includes a radiation source 12 and a detection element 14, separated by an angle $\alpha$.

An optical barrier 16 prevents radiation emitted by the radiation source 12 from reaching the detection element 14 directly. A sampling region 18 is located approximately centrally within the detector 10, and is arranged such that radiation from the radiation source 12 is incident directly into the region.

When clean, or substantially clean, air is present within the sampling region 18, radiation from the radiation source 12 passes through the sampling region 18, with little of the radiation being scattered as a result of interaction between the radiation and particulates in the sampling region. However, when larger particulates, such as smoke, steam or dust particulates are present within the sampling region 18, more of the radiation incident into the sampling region is scattered rather than passing directly through. A proportion of the radiation scattered from particulates in the sampling region 18 will be scattered in the direction of the detection element 14. A lens 20 may be positioned in front of the detection element 14, supported by lens supports 22a, 22b. The lens 20 would be arranged to direct any scattered radiation passing between the lens supports 22a, 22b directly towards the detection element 14. It will be apparent to a person skilled in the art that the detector would function correctly without the lens 20 and that, therefore, this is a non-essential, but preferred feature. For radiation of a particular wavelength or waveband, the angle through which the radiation is scattered is proportional to the size of the particulate from which it is scattered. Therefore, by using radiation having two distinct wavebands, which is scattered through a known angle, it is possible to distinguish between particulates of two different sizes.

Figure 2:
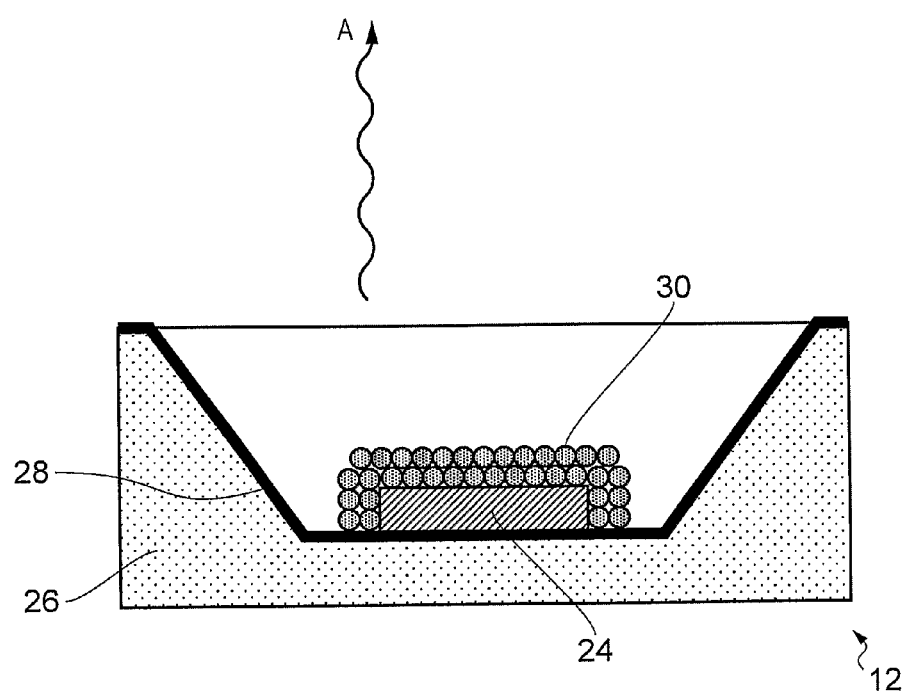
FIG. 2 is a detailed side elevation of a radiation source constructed in accordance with the invention.

FIG. 2 shows, in greater detail, the radiation source 12 which is constituted by a light emitting diode (LED) 24 secured to a base 26. The LED 24 is powered by a known power means (not shown). A reflective coating 28 is applied to the upper surface of the base 26 to reflect as much of the emitted radiation as possible in a forwards direction, i.e. in the direction of arrow A. The LED 24 has a coating 30 of phosphor particles, although it will be apparent to a person skilled in the art that, instead of a coating, a filter-like layer of phosphor could be positioned in front of the LED 24. The phosphor coating 30 absorbs some of the radiation emitted by the LED 24, and allows some of the radiation to pass directly through the coating towards the sampling region 18. A short time after the absorption takes place, the phosphor coating 30 emits radiation in a particular waveband, depending on the phosphor used. The effect of the re-emission of the radiation after the emission from the LED 24 is that a temporal separation is created between the two emissions. By temporal separation, it is meant that the second emission, in this case from the phosphor coating 30, occurs at a time slightly later than the emission from the LED 24. The reflective coating 28 ensures that a substantial proportion of the radiation emitted from the phosphor coating 30 is directed in the forwards direction A.

In the present embodiment of the invention, a blue LED 24 is used, that is the LED emits radiation having a waveband of approximately 475 nm. Blue LEDs are highly efficient, and emit radiation in a waveband sufficiently different to infrared radiation to achieve good discrimination between particulates of different sizes. It will be apparent to a person skilled in the art that radiation having a different waveband would also be suitable. Preferably, the waveband of the emitted radiation will be greater than approximately 200 nm. The phosphor coating 30 has an absorption band which substantially coincides with the energy emission band of the LED 24, preferably absorbing in the 400 nm to 500 nm range. The phosphor coating 30 re-radiates radiation in the infrared region, preferably in a range from around 870 nm to around 910 nm. Therefore, radiation is emitted from the radiation source 12 in two distinct wavebands.

Figure 3:
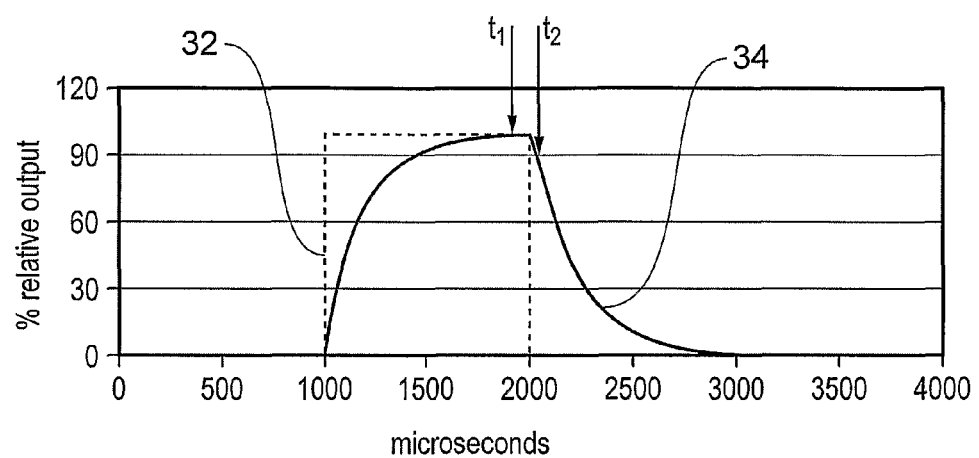
FIG. 3 is a graph showing relative emissions of radiation in two different wavebands from the radiation source of FIG. 2.

FIG. 3 shows the relative output of a phosphor coating 30 emitting radiation in the infrared region, following excitation by a blue LED. The square pulse 32, denoted by a dashed line, represents the emission from the LED 24, which is switched on at 1000 µs, and switched off at 2000 µs. The solid line 34 represents the emission from the phosphor coating 30. The radiation emitted gradually increases over the period of the LED pulse, and reaches a maximum at 2000 µs. At 2000 µs, when the LED 24 is switched off, the only emission is from the phosphor coating 30, so that the emission rapidly decreases in intensity. It is clear from FIG. 3 that a temporary overlap exists in the emissions; that is a period of time when radiation in both wavebands is being emitted by the radiation source 12. By measuring the signal at a time just before the square pulse 32 ends, and again just after the square pulse ends, it is possible to determine the contributions from each of the emissions 32, 34. Furthermore, since the measurements can be made over a very short time period, for example 200 µs apart, the particulates in the sampling region are unlikely to have moved far. Therefore, the scattered radiation is likely to be a result of scattering from the same volume in the sampling region.

The result of detecting radiation at two different wavebands is that a distinction can be made between particulates of different sizes. The amplitude of the detected signal represents the quantity of particulates dispersed in the sampling region 18. The ratio of amplitudes of the signal detected at two different times, $t_1$ and $t_2$, as shown in FIG. 3, provides information about the relative spread of the sizes of the particulates in the sampling region 18. With this information, it is possible to distinguish between the sources of the particulates, for example, it is possible to distinguish between particulates of aerosol spray and smoke from, say, burning paper.

In use, electrical energy is supplied to the radiation source 12 by any one of many known methods. The radiation source 12 emits radiation in a first waveband, as a result of an electrical pulse to the LED 24. A proportion of this radiation is absorbed by the phosphor coating 30, which then emits radiation in a second waveband. The radiation that is not emitted by the phosphor coating 30 is directed towards the sampling region 18, along with the radiation emitted by the phosphor coating. If smoke particulates, or any other particulates of a size relatively large compared to clean air particles, are present in the sampling region 18, then some of the radiation will be scattered from those particulates at an angle β (see FIG. 1) from the original direction of incidence of the radiation. The scattered radiation passes through the lens 20, and is detected by the detection element 14. The signal received by the detection element 14 is processed by a processor (not shown). The processor can be arranged to process the information in a number of ways, depending on the signal received by the detection element 14. In particular, if the signal received by the detection element 14 is a result of a combination of the radiation emitted by the LED 24 and by the phosphor coating 30, then the processor will need to be arranged to deconvolve the signal so as to determine the contribution from the radiation in each distinct waveband. The signal resulting from the combination of radiation from the LED 24 and the phosphor coating 30 can be compared to a predetermined signal profile, obtained from experimental measurements taken from a range of scattering conditions.

Alternatively, if details are known of the exact time that the LED 24 is switched on and off, and of the times at which readings at the detection element 14 are taken, then it is possible to deconvolve the resultant signal, and obtain information relating to the scattered signal for radiation in each distinct waveband individually.

A suitable detection element 14 for use in the invention is a broadband photodiode, such as VTP100CH, manufactured by Perkin Elmer. If a broadband photodiode is used, then one can achieve a finer discrimination between the received signals, and can overcome noise by adding a filter, or a combination of filters to the photodiode. Alternatively, the detection element could comprise an arrangement of tuned photodiodes collated in a single package, such that the overall response of the detection element peaks in sensitivity at the desired wavebands.

Ideally, the detection element 14 has a good response to radiation of both wavebands. If the response of the detection element 14 is more sensitive in the infrared region, then, if an infrared emitting phosphor is used, smaller quantities of phosphor are required.

The detection element 14 is in communication with the power means (not shown) of the radiation source, enabling readings to be taken at precise moments relative to the emissions taking place. The time-separated signals received by the detection element 14 can be analysed by a number of methods. One method is to provide a switched output from the detection element 14, the switch being activated by the pulse that powers the radiation source 12. This would ensure that a suitable time delay exists between the detection of each signal.

In an alternative embodiment, it is envisaged that the detector 10 includes a processor (not shown) for processing information received by the detection element 14.

Figure 4:
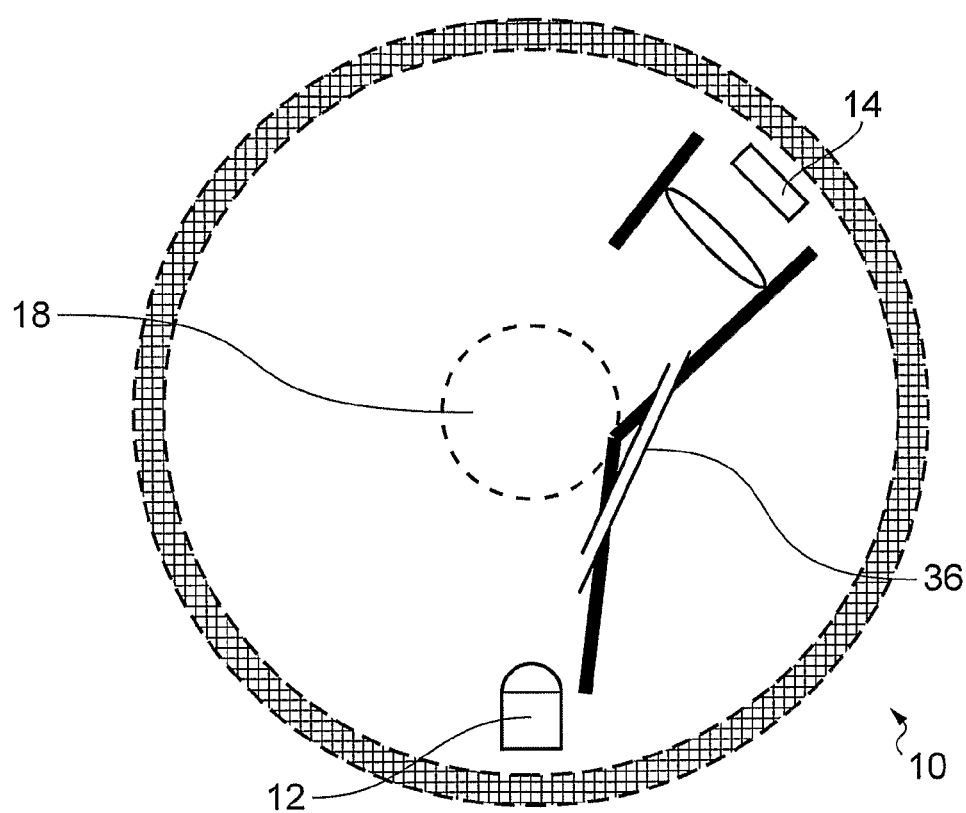
FIG. 4 is a schematic diagram of a detector constructed in accordance with a second embodiment of the invention.

FIG. 4 shows an optical scatter detector 10 constructed in accordance with a second embodiment of the invention. The detector 10 includes a radiation source 12 and a detection element 14, separated by an optical barrier 16, as in the detector of FIG. 1. However, in this embodiment, the detector 10 further includes an optical bleed channel 36, arranged to enable a proportion of the radiation emitted by the LED 24 and by the phosphor coating 30 to pass directly to the detection element 14. It will be apparent to a person skilled in the art that the 'bleeding' of radiation directly to the detection element 14 could alternatively be achieved, for example, by reflecting the radiation around the sampling region 18, or through an optical fibre. The optical bleed channel 36 ensures that there is optical continuity and electrical continuity through the detector, that is, that both the radiation source 12 and the detection element 14 are in optical and electrical communication and that they are both functioning correctly. By taking measurements of the signal received directly from the radiation source 12 through the optical bleed channel 36, where it can be assumed that there is clean air, and no impurities such as smoke, dust or steam, then it is possible to take into account any changes that occur in the LED 24 or the phosphor coating 30 over time. Such changes are likely to occur as a result of degradation of the LED 24 or the phosphor coating 30. This provides a means for verifying over a period of time that the ratio of the signals at different wavebands remains constant and, if necessary, can be calibrated. Since the optical bleed channel 36 is positioned between the radiation source 12 and the detection element 14, equal amounts of radiation from the LED 24 and from the phosphor coating 30 will be transmitted to the detection means.

Figure 5:
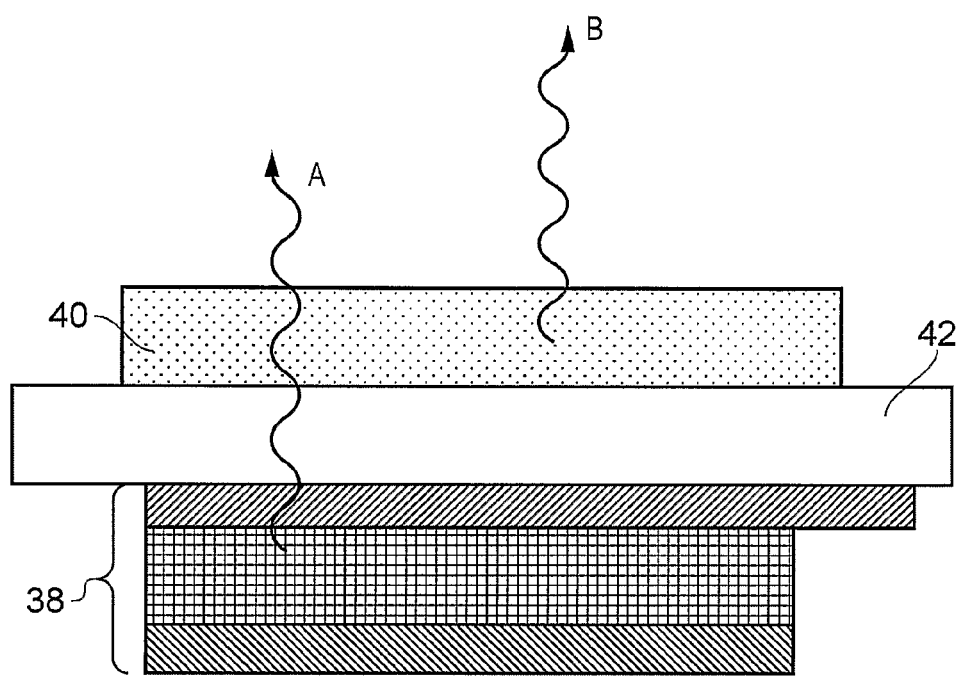
FIG. 5 is a schematic diagram of a part of the detector shown in FIGS. 1 and 4, constructed in accordance with a third embodiment of the invention.

In a third embodiment of the invention, the radiation source 12 utilises photon-recycling to produce the radiation in a second waveband, from the radiation emitted in a first waveband. FIG. 5 shows an arrangement whereby photon-recycling is utilised. This arrangement provides an alternative way of producing radiation having wavebands in two distinct wavebands. Instead of having a phosphor-coated LED 24, in this arrangement, a first LED 38 is powered electrically using standard electrical power means (not shown) and emits radiation in the direction of arrow A having a waveband in the blue region. A second LED 40 is separated from the first LED 38 by a spacer 42. The spacer 42 is made from a transparent insulating material or from a semiconductor material having a large band gap. Some of the radiation emitted by the first LED 38 passes through the second LED 40 in the direction of the arrow A. Some of the radiation emitted by the first LED 38 is absorbed by the second LED 40. As a result of the photoelectric effect, this absorbed radiation is used to power the second LED 40. The second LED 40 emits radiation having a longer waveband, in the infrared region, and this radiation is emitted in the direction of the arrow B. To achieve a temporal separation between the emission of the first LED 38 and the second LED 40, an optical delay line (not shown) exists between the two LEDs. The optical delay line introduces a uniform delay between the emissions of the two LEDs, such that both emissions are square pulses.

Figure 6:
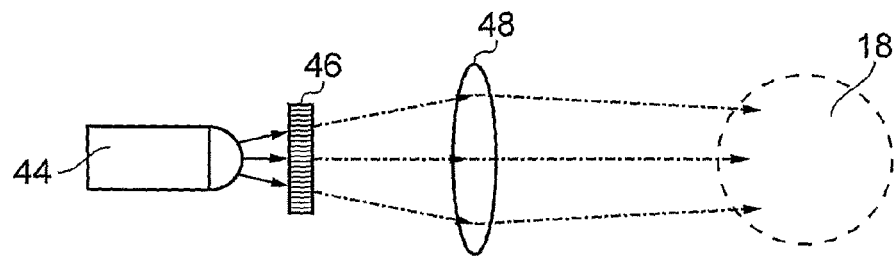
FIG. 6 is a schematic diagram of a part of the detector shown in FIGS. 1 and 4, and constructed in accordance with a fourth embodiment of the invention.

FIG. 6 shows another arrangement using photon-recycling, in accordance with a fourth embodiment of the invention. In this embodiment, a first LED 44 is arranged to emit radiation having a waveband in the blue region, in the direction of a semiconductor structure 46, which includes a second LED (not shown). In a process similar to that shown in FIG. 5, some of the radiation emitted by the first LED 44 is used to power the second LED in the semiconductor structure 46, and some of the radiation passes through the semiconductor structure towards the sampling region 18. The second LED emits radiation having a waveband in the infrared region. The radiation emitted by both the first LED 44 and the second LED passes through a lens 48, which directs the radiation towards the sampling region 18. To ensure the radiation in each waveband is emitted separately, a delay means is employed to create a delay between the emission from the first LED 44 and the second LED.

Figure 7:
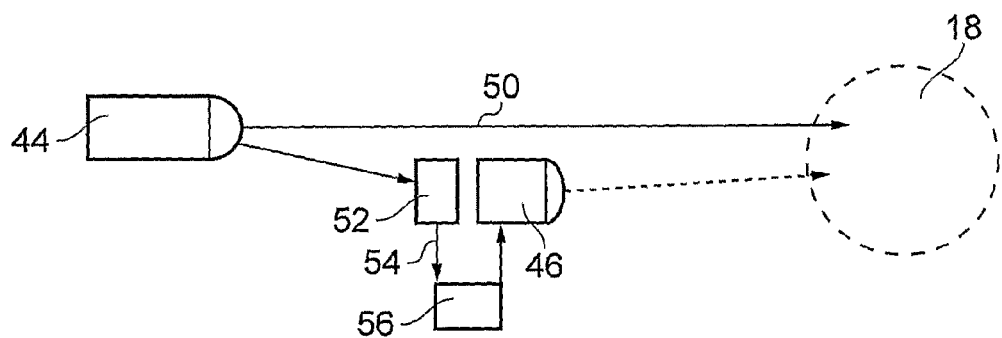
FIG. 7 is a schematic diagram of a part of the detector shown in FIGS. 1 and 4, constructed in accordance with a fifth embodiment of the invention.

In FIG. 7, a fifth embodiment of the invention is shown. Again, photon-recycling is used. In this embodiment, the first LED 44 is powered by a known power supply means (not shown). Some of the emitted radiation is directed towards a photoexcitation element 52. The rest of the emitted radiation, denoted by arrow 50, is directed towards the sampling region 18 without passing through the photoexcitation element 52. The emitted radiation causes electrons 54 to be emitted by the photoexcitation element 52. The emitted electrons 54 are stored in a storage element 56, and the current passes through a network of resistors and capacitors (not shown) to a second LED 46, which is powered by the current. The passage of the current 54 through the network of resistors and capacitors causes a delay between the emission of radiation from the first LED 44 and the emission of radiation from the second LED 46.

Figure 8:
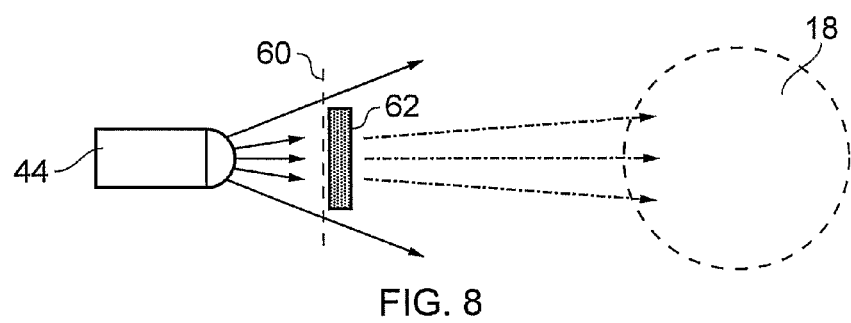
FIG. 8 is a schematic diagram of a part of the detector shown in FIGS. 1 and 4, and constructed in accordance with a sixth embodiment of the invention.

A sixth embodiment of the invention is shown in FIG. 8. An LED 44 emits radiation having a waveband in the blue region towards a dichroic mirror 60 having a phosphor coating 62 formed thereon. The dichroic mirror 60 allows radiation having a waveband in the blue region to pass through, but reflects radiation having a waveband in the infrared region. Therefore, the 'blue' radiation emitted from the LED 44 passes through the dichroic mirror 60, and some of this radiation is able to pass through the phosphor coating 62 towards the sampling region 18. The remainder of the radiation is absorbed by the phosphor coating 62, and this causes the phosphor coating to emit infrared radiation. Some of the infrared radiation is emitted in the direction of the sampling region 18. Radiation that is emitted in the direction of the dichroic mirror 60 is reflected towards the sampling region 18.

Figure 9:
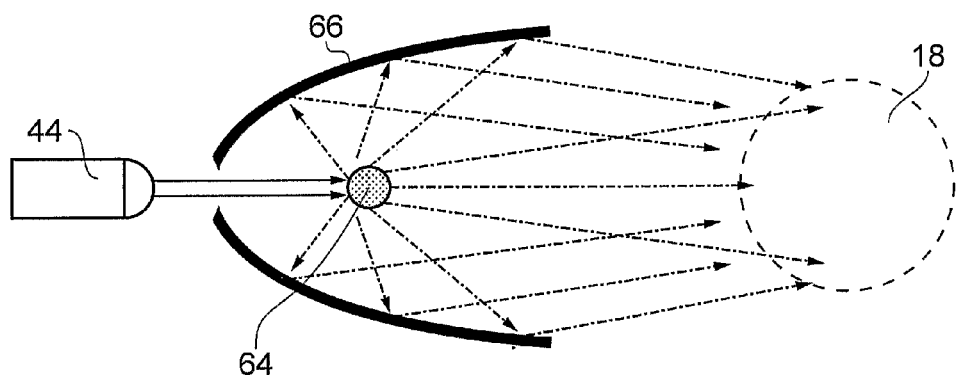
FIG. 9 is a schematic diagram of a part of the detector shown in FIGS. 1 and 4, and constructed in accordance with a seventh embodiment of the invention.

A similar arrangement is shown in FIG. 9, which exemplifies a seventh embodiment of the invention. An LED 44 emits radiation having a waveband in the blue region towards a phosphor target 64, which is located approximately at the focus of a parabolic mirror 66. Some of the 'blue' radiation passes through the phosphor target 64 towards the sampling region 18, and the remaining radiation is absorbed by the phosphor target. The phosphor target 64 emits infrared radiation in all directions, and the mirror 66 causes the infrared radiation to be directed towards the sampling region 18.

Figure 10:
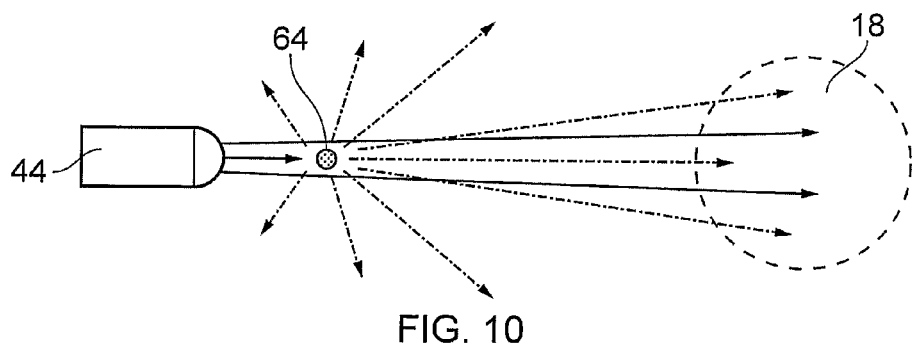
FIG. 10 is a schematic diagram of a part of the detector shown in FIGS. 1 and 4, and constructed in accordance with an eighth embodiment of the invention.
Figure 11:
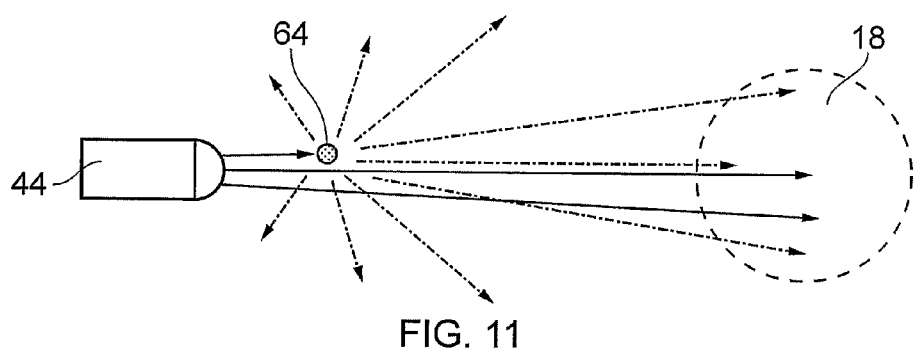
FIG. 11 is a schematic diagram of a part of the detector shown in FIGS. 1 and 4, demonstrating an alternative construction, in accordance with an eighth embodiment of the invention.
Figure 12:
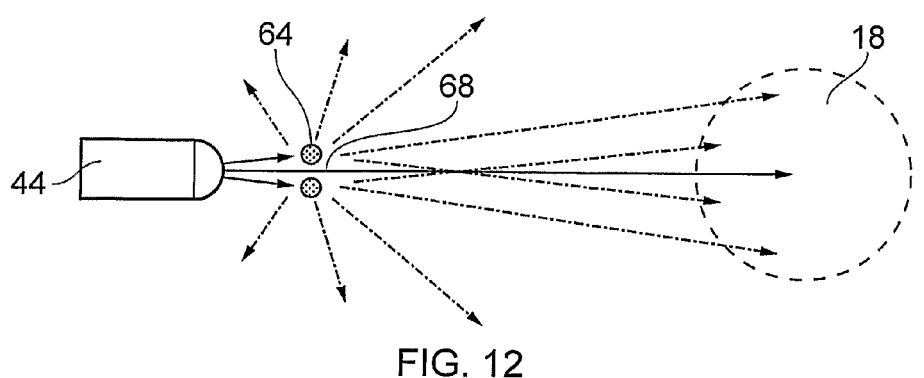
FIG. 12 is a schematic diagram of a part of the detector shown in FIGS. 1 and 4, demonstrating another alternative construction, in accordance with an eighth embodiment of the invention.

In FIGS. 10, 11 and 12, three arrangements of an eighth embodiment of the invention are shown. In each of these arrangements, an LED 44 emits radiation, having a waveband in the blue region, in the direction of the sampling region 18. A phosphor target 64 is positioned in the path of the radiation, the phosphor target being arranged to absorb some of the radiation emitted by the LED 44, and then emit infrared radiation, some of which will be directed towards the sampling region 18. The radiation emitted by the LED 44 that is not absorbed by the phosphor target 64 passes to the sampling region 18. In FIG. 10, the 'blue' radiation passes either side of the phosphor target 64; in FIG. 11, the 'blue' radiation passes to one side of the phosphor target; and, in FIG. 12, the 'blue' radiation passes through an aperture 68 in the phosphor target.

Figure 13:
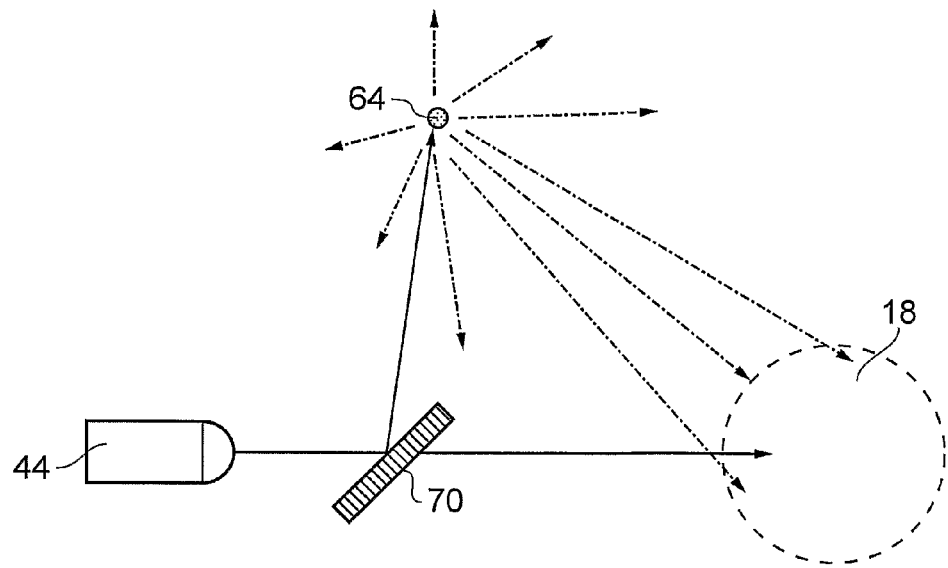
FIG. 13 is a schematic diagram of a part of the detector shown in FIGS. 1 and 4, and constructed in accordance with a ninth embodiment of the invention.

A ninth embodiment of the invention is shown in FIG. 13. In this arrangement, an LED 44 emits radiation having a waveband in the blue region towards a partially-reflective mirror 70. Some of the radiation is transmitted through the mirror 70 towards the sampling region 18. The rest of the radiation is reflected towards a phosphor target 64, which absorbs the 'blue' radiation, and emits infrared radiation, some of which is directed towards the sampling region 18. It will be apparent to a person skilled in the art that, in this embodiment, the reflective mirror 70 could be replaced with any other suitable component, such as a beam splitter, a refractive component, or a light guide.

Figure 14:
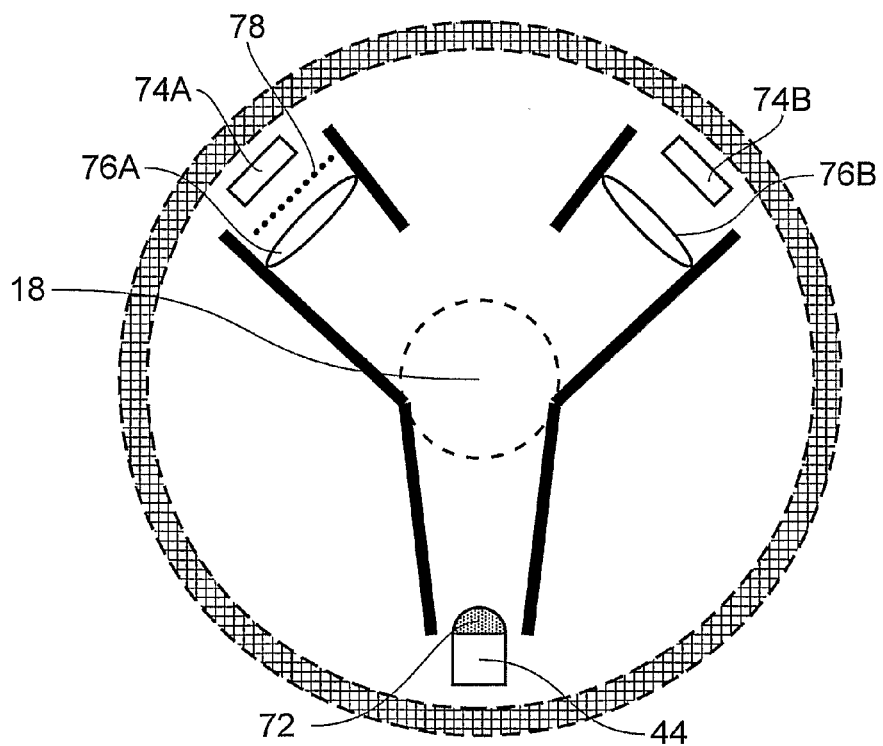
FIG. 14 is a schematic diagram of a detector constructed in accordance with a tenth embodiment of the invention.

FIG. 14 shows an arrangement in accordance with a tenth embodiment of the invention. An LED 44 has a phosphor coating 72 formed thereon. The LED 44 emits radiation having a waveband in the blue region towards the sampling region 18. When particles larger than air particulates, for example, smoke, steam or dust, are present within the sampling region 18, some of the radiation is scattered towards detection elements 74A, 74B. The scattered radiation passes through lenses 76A, 76B, which are positioned adjacent to respective detection elements 74A, 74B. An optical filter 78 is positioned in front of one of the detection elements 74A, and is arranged to distinguish between the 'blue' radiation resulting from the radiation emitted by the LED 44, and the infrared radiation emitted by the phosphor coating 72.

Figure 15:
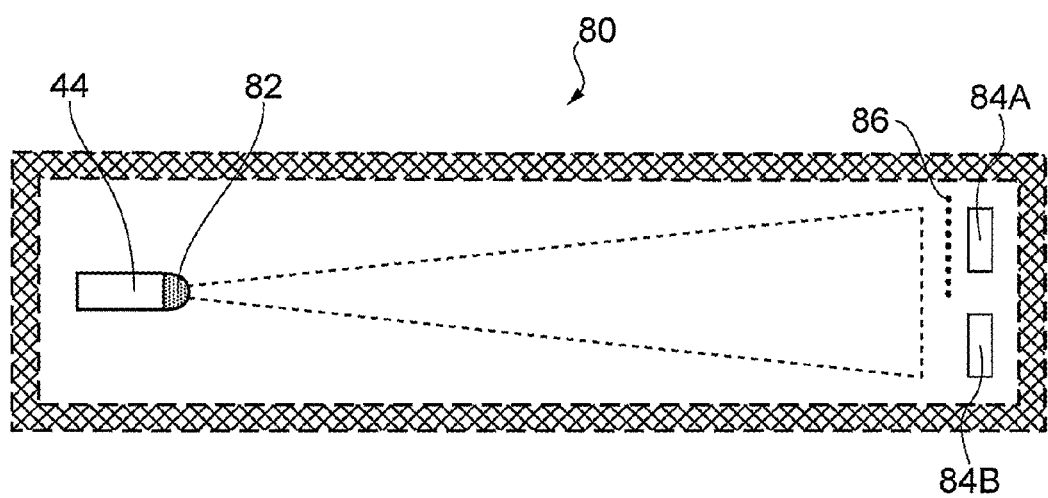
FIG. 15 is a schematic diagram of a detector constructed in accordance with an eleventh embodiment of the invention.

FIG. 15 shows a transmission detector 80 constructed in accordance with an eleventh embodiment of the invention. The transmission detector 80 measures radiation that is not scattered by non-air particulates. The detector 80 includes an LED 44 having a phosphor coating 82 formed thereon. The LED 44 emits radiation having a waveband in the blue region towards two detection elements 84A, 84B. Some of the emitted radiation is absorbed by the phosphor coating 82, and some passes through the coating towards the detection elements 84A, 84B. The phosphor coating 82 emits infrared radiation, some of which is directed towards the detection elements 84A, 84B. An optical filter 86 is positioned in front of one of the detection elements 84A, and is arranged to distinguish between the 'blue' radiation resulting from the radiation emitted by the LED 44, and the infrared radiation emitted by the phosphor coating 82. By comparing the emissions detected in clean air, with the emissions detected when smoke or similar larger particulates are present in the device, it is possible to determine what type of particulates are present.

Figure 16:
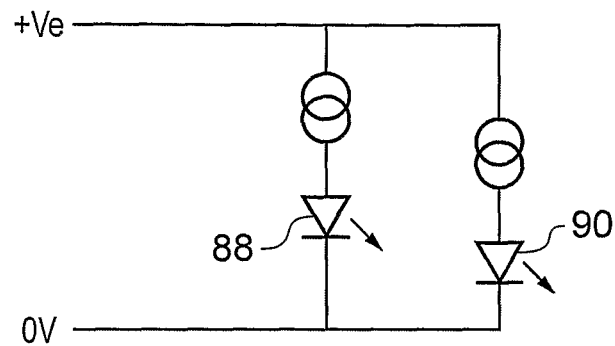
FIG. 16 is a circuit diagram of an arrangement suitable for use in any of the embodiments of the invention.

FIG. 16 shows an arrangement that can be implemented into any of the embodiments of the invention described hereinbefore, in place of the radiation sources previously shown. The arrangement provides an alternative way of creating a temporal difference between the emission of 'blue' radiation and the emission of infrared radiation. A 'blue-emitting' LED 88 and an infrared-emitting LED 90 are arranged in parallel, and are powered by a common power source. The arrangement utilises the different actuating voltages provided to the LEDs 88, 90 to create the temporal difference. The effect of arranging the LEDs 88, 90 in this way is that the 'blue-emitting' LED 88 emits radiation for a shorter time than the infrared LED 90.

Figure 17:
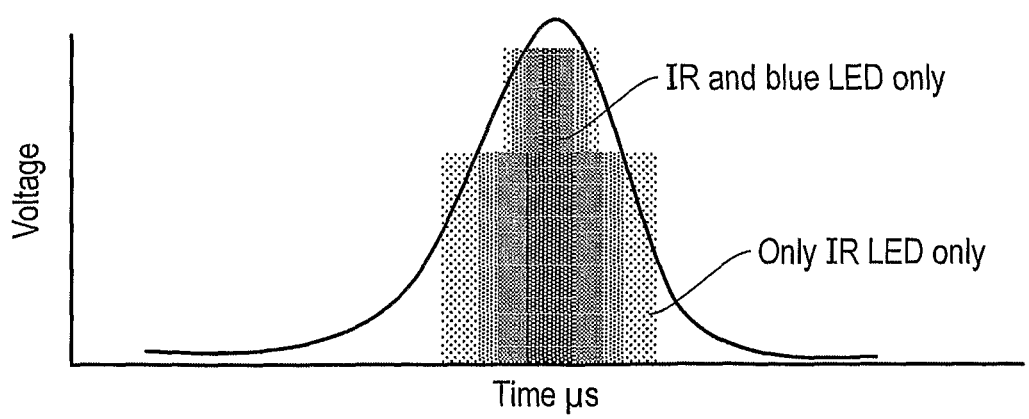
FIG. 17 is a graph showing the temporal difference in emissions from two radiation sources.

The graph shown in FIG. 17 demonstrates the temporal difference in emissions from the two LEDs 88, 90 as the voltage supplied to the LEDS is varied over time. The infrared-emitting LED 90 emits for a relatively long period, whereas both LEDs 88, 90 emit simultaneously for a short period time. Thus, it is possible to distinguish between the emissions from each of the LEDS 88, 90, without using a phosphor coating, or a phosphor target.

The detector is typically used as part of a detector system, in which, a number of detectors are connected to a control unit. The control unit supplies power to the detectors, receives the output signal from the detection element 14 of each detector, and analyses the received signal. In response to the received signal, the control unit performs an operation, for example activating an alarm. Alternatively, each detector in the system may be provided with its own control unit.

To process the signals received by the control unit, the ratio of the amplitude of radiation in each waveband is calculated. The ratios differ depending on the source of the particulate from which the radiation is scattered. The calculated ratio is compared with known ratios in a lookup table, the known ratios relating to scattered signals from known sources, for radiation in particular wavebands. Using this method, the control unit can rapidly determine the most likely source of particulates causing the scattering. Since the determination of a probable source will not always be accurate, the control unit is configured to decide how to interpret the signal, that is to determine whether or not the determination has been accurately made. In some applications of such a system, it is important to have fewer inaccurate determinations of a particulate source. In others, an inaccurate determination may not be so important. The control unit can, therefore, be programmed to respond accordingly.

In an example where the detector system is used as a fire detection system, the analysis of the signals received leads to a determination of either a genuine fire source or not. In such a case, additional parameters are analysed to increase the accuracy of the determination made. For example, the control unit also monitors how the amplitude of each signal, and the ratio of the signals, behave over time. If the particulates causing the scattering are from steam, then the ratio of the amplitudes is likely to be very different to that of smoke. Additionally, the individual amplitudes of the signals and the ratio of the signals will vary over time differently for steam than for smoke. Furthermore, where scattering is caused by steam, saturation of the signal can occur. The steam dissipates rapidly after the saturation occurs, and this behaviour can be used in addition to the received signals to determine the source of the particulates causing the scattering.

In addition to measuring the scattering of radiation, a detector can be combined with one or more other sensors, for example a heat sensor, a gas sensor, or a moisture sensor. If signals from these types of sensor are combined with signals from a particulate detector of the sort described herein, a more accurate determination of the source of the particulates can be made.

An alternative method of processing data from multiple sensors is to employ a fuzzy logic system, with a determination based on the outcome of the fuzzy logic algorithm.

Other systems may be incorporated into the detector system to improve safety and accuracy of the determination made. For example, in a detector incorporating a particulate sensor, a heat sensor and a gas sensor, if the gas sensor fails for any reason, the control unit could be programmed to operate using results received from only the heat sensor and the particulate sensor.

In addition, the detector system could be programmed to utilise 'near neighbour' results to improve determination of whether or not an alarm is required. For example, if one detector in a system outputs a signal indicating an uncertainty as to whether or not smoke is a source of scattering, signals from other detectors in the vicinity may be combined to improve the accuracy.

It will be apparent to a person skilled in the art that various modifications could be made to the detector 10 hereinbefore described, which fall within the scope of the appended claims.

The radiation source 12 could include an incandescent filament bulb (not shown) instead of an LED 24. In an incandescent filament bulb, the waveband of the radiation emitted becomes shorter as the temperature of the filament increases after it has been switched on. Therefore, since a temporal separation exists between the "blue" and "infrared" radiation, an incandescent filament bulb could be used in the radiation source.

Although the description herein refers generally to emissions in first and second wavebands, one or more further emissions in alternative wavebands could be made and detected, and used in the signal analysis. For example, in an embodiment where a phosphor coating is applied to an LED, a second phosphor coating could be added to the LED, arranged to emit radiation in a third waveband. In an alternative example, in an embodiment in which two LEDs are used to emit radiation in two predetermined wavebands, a phosphor coating could be applied to one, or both of the LEDs, to generate additional emissions in third and/or fourth wavebands.

It will be apparent to a person skilled in the art that, if emissions are made in more than two wavebands, it will be necessary to take measurements at more than two instances.

In FIG. 3, measurements are shown to be taken at instances $t_1$ and $t_2$, immediately before and after the end of the square pulse emission from the LED. However, a person skilled in the art will appreciate that the two measurements could be taken at any other instances during the emissions, as long as one of the measurements is taken during the overlap of the emissions in the two wavebands, and the other is taken when there is no overlap of the emissions in the two wavebands. It will also be appreciated that, to reduce the amount by which the particulates in the sample move between the two measurements being taken, the time between taking the two measurements will be kept as short as possible. Measurements may be taken at more than two instances, for example at a third instance, $t_3$, and at a fourth instance, $t_4$. The additional measurements taken at these instances could then be used in the signal processing that takes place in the processor, to obtain a more accurate determination of the type of particulates, or the characteristics of the particulates, detected.

In practice, the detector 10 will be used to emit and detect radiation having wavebands in the optical region including the infrared and ultraviolet regions. However, it will be apparent to a person skilled in the art that the detector could function using radiation in other regions of the electromagnetic spectrum.

The term "waveband" referred to herein is intended to mean a narrow band of wavelengths.

The invention claimed is:

1. A particulate detector comprising:
   a radiation source arranged to emit radiation in at least first and second predetermined wavebands towards a sampling region; and
   a detection element arranged to detect radiation from the sampling region at at least first and second instances;
   wherein the radiation source is such that the emissions in the at least first and second predetermined wavebands temporarily overlap;
   wherein the detector is such that, at the instances at which the radiation is detected, the relative contributions from the emissions in each predetermined waveband are distinguishable, thereby allowing characteristics of particulates in the sampling region to be determined;
   wherein the radiation emitted in the first predetermined waveband is emitted in a pulse; and
   wherein the first instance occurs after the start of the pulse but before the end of the pulse, and the second instance occurs after the end of the pulse.

2. A detector according to claim 1, wherein the pulse is a square pulse.

3. A detector according to claim 1, further comprising a processor arranged to process information about the radiation received by the detection element.

4. A detector according to claim 1, wherein the radiation source comprises a light emitting diode for emitting radiation in the first predetermined waveband.

5. A detector according to claim 4, wherein the light emitting diode is arranged to emit radiation having a waveband in the range 450 nm to 500 nm.

6. A particulate detector comprising:
   a radiation source arranged to emit radiation in at least first and second predetermined wavebands towards a sampling region; and
   a detection element arranged to detect radiation from the sampling region at least first and second instances;
   wherein the radiation source is such that the emissions in the at least first and second predetermined wavebands temporarily overlap;
   wherein the detector is such that, at the instances at which the radiation is detected, the relative contributions from the emissions in each predetermined waveband are distinguishable, thereby allowing characteristics of particulates in the sampling region to be determined; and
   wherein the radiation source further comprises a phosphor layer arranged to absorb a proportion of the radiation in the first predetermined waveband, and to emit radiation in the second predetermined waveband.

7. A particulate detector comprising:
   a radiation source arranged to emit radiation in at least first and second predetermined wavebands towards a sampling region; and
   a detection element arranged to detect radiation from the sampling region at least first and second instances;
   wherein the radiation source is such that the emissions in the at least first and second predetermined wavebands temporarily overlap;
   wherein the detector is such that, at the instances at which the radiation is detected, the relative contributions from the emissions in each predetermined waveband are distinguishable, thereby allowing characteristics of particulates in the sampling region to be determined;
   wherein the radiation source further comprises a second light emitting diode for emitting radiation in the second predetermined waveband; and
   wherein the radiation source is arranged such that radiation emitted in the first redetermined waveband is used to power the second light emitting diode.

8. A detector according to claim 1, further comprising an optical bleed channel for enabling radiation emitted by the radiation source to pass directly to the detection element.

9. A detector according to claim 1, wherein the detector is a scatter detector.

10. A detector according to claim 1, wherein the detector is a transmission detector.

11. A detector system comprising a control unit and a plurality of particulate detectors, each particulate detector comprising:
    a radiation source arranged to emit radiation in at least first and second predetermined wavebands towards a sampling region; and
    a detection element arranged to detect radiation from the sampling region at least first and second instances;
    wherein the radiation source is such that the emissions in the at least first and second predetermined wavebands temporarily overlap;
    wherein the detector is such that, at the instances at which the radiation is detected, the relative contributions from the emissions in each predetermined waveband are distinguishable, thereby allowing characteristics of particulates in the sampling region to be determined; and wherein the radiation source further comprises a phosphor layer arranged to absorb a proportion of the radiation in the first predetermined waveband, and to emit radiation in the second predetermined waveband.

12. A system according to claim 11, wherein the control unit is arranged to supply power to, and receive signals from, each detector.

13. A system according to claim 11, wherein the control unit is arranged to receive signals from at least one additional detection device.

14. A system according to claim 13, wherein the control unit is arranged to combine information received from the or each additional detection device with information received from at least one of the detectors.

15. A system according to claim 13, wherein each additional detection device is one of the following group: a heat sensor; a gas sensor; a moisture sensor.

* * * * *

UNITED STATES PATENT AND TRADEMARK OFFICE
CERTIFICATE OF CORRECTION

PATENT NO. : 8,559,006 B2
APPLICATION NO. : 13/121467
DATED : October 15, 2013
INVENTOR(S) : Stephen John Penney et al.

Page 1 of 1

It is certified that error appears in the above-identified patent and that said Letters Patent is hereby corrected as shown below:

In the Claims:

Column 12
Claim 6
Line 12
Whereas, "sampling region at least first and second instances;"
should be corrected to read, "sampling region at at least first and second instances;"

Signed and Sealed this
Twenty-fourth Day of December, 2013

Margaret A. Focarino
*Commissioner for Patents of the United States Patent and Trademark Office*